US008383167B2

(12) United States Patent
Corstjens et al.

(10) Patent No.: US 8,383,167 B2
(45) Date of Patent: Feb. 26, 2013

(54) METHOD FOR COSMETICALLY TREATING CASPASE-14 DEFICIENCY

(75) Inventors: Hugo A. Corstjens, Maaseik (BE); Lieve Declercq, Ekeren (BE); Gerry Eyckmans, Geel (BE); Luc F. J. Van Overloop, Antwerp (BE)

(73) Assignee: ELC Management, LLC, New York, NY (US)

( * ) Notice: Subject to any disclaimer, the term of this patent is extended or adjusted under 35 U.S.C. 154(b) by 22 days.

(21) Appl. No.: 13/042,915

(22) Filed: Mar. 8, 2011

(65) Prior Publication Data

US 2012/0230926 A1    Sep. 13, 2012

(51) Int. Cl.
*A01N 65/00* (2009.01)
(52) U.S. Cl. ...................................... 424/725
(58) Field of Classification Search ................. None
See application file for complete search history.

(56) References Cited

U.S. PATENT DOCUMENTS

| 7,771,925 | B2 | 8/2010 | Hendrix et al. |
| 2004/0234480 | A1 | 11/2004 | Pauly et al. |
| 2005/0271751 | A1 | 12/2005 | Perrier et al. |
| 2006/0257509 | A1 | 11/2006 | Zimmerman et al. |
| 2009/0123572 | A1 | 5/2009 | Hibino et al. |
| 2010/0166814 | A1 | 7/2010 | Dumas et al. |
| 2010/0173957 | A1 | 7/2010 | Jacobson et al. |

FOREIGN PATENT DOCUMENTS

| DE | 102008035834 | 2/2010 |
| EP | 1859806 | 11/2007 |
| JP | 2009-242333 | 10/2009 |
| JP | 2009242333 | 10/2009 |
| JP | 2010-235559 | 10/2010 |
| KR | 20030069659 | 8/2003 |
| KR | 2008-0096132 | 10/2008 |
| WO | 2008/025830 | 3/2008 |
| WO | 2008/106177 | 9/2008 |

OTHER PUBLICATIONS

Amstad, et al.; Product Application Focus: Detection of Caspase Activation In Situ by Fluorochrome-Labeled Caspase Inhibitos; BioTechniques; vol. 31; No. 3; pp. 608-616; 2001.

Presland, Richard B.; Review; function of Filaggrin and Caspase-14 in Formation and Maintenance of the Epithelial Barrier; Dermatol Sinica; Dept. of Oral Biology; School of Dentistry and Division of Dermatology; Dept. of Medicine; University of Washington, Seatttle; pp. 1-14; 2009.
"Natural Homeremedies for Life: Home Remedies for Dry Skin"; http://web.archive.org/web.archive.org/web/20091120181532/ http://www.natural-homeremedies-for-life.com/home-remedies-for-dry-skin.html#. (Jun. 2012).
Supplementary European Search Report; Applic. No. EP11158482; Completion Date: Jan. 4, 2012; Date of Mailing: Jan. 20, 2012.
Georgetti, et al.; "Evaluation of the antioxidant activity of soybean extract by different in vitro methods and investigation of this activity after its incorporation in topical formulations"; European Journal of Pharmaceutics and Biopharmaceutics, Elsevier Science Publishers B.V.; Amsterdam, NL; vol. 64; No. 1; pp. 99-106; Aug. 2006.
Hsu, et al.; "Chemopreventive effects of green tea polyphenol is associated with caspase 14 induction in epidermal keratinocytes"; Proceedings of The American Association For Cancer Research Annual Meeting; vol. 45; (1 page); Mar. 2004.
Hsu, et al.; "Green tea polyphenols reduced psoriasiform lesions in a mouse model for human psoriasis in association with caspase 14 activation"; Journal of Investigative Dermatology; vol. 127; No. Suppl. 1; p. S8; Apr. 2007.
Denecker, et al.; "Caspase-14 protects against epidermal UVB photodamage and water loss"; Nature Cell Biology; Nature Publishing Group, GB; vol. 9; No. 6; pp. 666-674; May 2007.
PCT International Search Report; International Applic. No. PCT/US2012/027676; Completion Date: Sep. 26, 2012; Mailing Date: Sep. 26, 2012.
PCT International Search Report; International Applic. No. PCT/US2012/027702; Completion Date: Sep. 27, 2012; Mailing Date Sep. 27, 2012.
PCT Written Opinion; International Applic. No. PCT/US2012/027676; Completion Date: Sep. 26, 2012; Mailing Date: Sep. 26, 2012.
PCT Written Opinion; International Applic. No. PCT/US2012/027702; Completion Date: Sep. 27, 2012; Mailing Date: Sep. 27, 2012.

*Primary Examiner* — Michael Meller
(74) *Attorney, Agent, or Firm* — Idris N. McKelvey (57) ABSTRACT

A method of cosmetic care comprising activating capsase-14 expression in skin deficient in caspase-14 expression by applying, on at least one skin zone in need thereof, an effective amount of a plant extract selected from the group consisting of *litchi*, glasswort, peach, soja seed, sweet basil, cucumber, chanterelle, leek, kiwi fruit, rhubarb, grapefruit, wheat, raspberry, plum, and mixtures thereof, to activate caspase-14 expression in said skin.

1 Claim, 10 Drawing Sheets

METHOD FOR COSMETICALLY TREATING CASPASE-14 DEFICIENCY

FIELD OF THE INVENTION

This invention relates to formulations and methods for improving hydration characteristics of skin. In particular, the formulations and methods herein relate to activation of caspase-14 expression in human skin.

BACKGROUND OF THE INVENTION

Skin is subject to deterioration through the passage of time (chronological aging, dermatological disorders, hormonal changes, environmental abuse (wind, air conditioning, heat, pollution, etc.) all of which may be accelerated by exposure of skin to radiation from the sun (photoaging). Consumers are increasingly seeking "anti-aging" cosmetic products which treat, or delay, the visible signs of chronological aging and photo-aging skin such as wrinkles, lines, sagging, hyperpigmentation and age spots. Cellulite also manifests itself as a result of increased adipogenicity and reduced connective tissue matrix.

Caspase-14 is a unique protease which controls maturation of the epidermis. This control results from proteolytic processing of filaggrin, a protein that is recognized as being involved in late stages of skin cell differentiation. The products of the action of caspase-14 on filaggrin prevent UVB photo damage, as well as water loss. While many cosmetic composition currently marketed are designed to treat signs of aging, none of the products and methods of treatment are directed to improved caspase-14 expression.

Accordingly, there is an ongoing need for a cosmetic composition for topical application to skin for treating deficiency and degradation of caspase-14 expression in human skin to prevent visible signs of aging such as wrinkles, lines, sagging, hyperpigmentation, and age spots.

SUMMARY OF THE INVENTION

The invention herein relates to a method for treating human skin comprising;
a) identifying a subject deficient in caspase-14;
   wherein said caspase-14 deficiency is identified by the presence of a skin condition selected from the group consisting of eczema, xerotic skin, and skin dryness in at least one skin zone of said subject; and
b) activating caspase-14 in human skin by administering to a subject in need thereof a therapeutically effective amount of a composition comprising one or more extracts selected from the group consisting of *litchi*, glasswort, peach, soja seed, sweet basil, cucumber, chanterelle, leek, kiwi fruit, rhubarb, grapefruit, wheat, raspberry, plum, and mixtures thereof.

Another aspect of this invention involves a method of cosmetically treating human skin comprising activating caspase-14 expression in skin deficient in caspase-14 expression by applying, on at least one skin zone in need thereof, an effective amount of a plant extract selected from the group consisting of *litchi*, glasswort, peach, soja seed, sweet basil, cucumber, chanterelle, leek, kiwi fruit, rhubarb, grapefruit, wheat, raspberry, plum, and mixtures thereof, to activate caspase-14 expression in said skin.

Another aspect of the invention involves one or more extracts selected from the group consisting of *litchi*, glasswort, peach, soja seed, sweet basil, cucumber, chanterelle, leek, kiwi fruit, rhubarb, grapefruit, wheat, raspberry, plum, and mixtures thereof, for use in topically treating caspase-14 deficiency in human skin.

Yet another aspect of the invention involves the use of one or more extracts selected from the group consisting of *litchi*, glasswort, peach, soja seed, sweet basil, cucumber, chanterelle, leek, kiwi fruit, rhubarb, grapefruit, wheat, raspberry, plum, and mixtures thereof, in the manufacture of a medicament for the treatment of caspase-14 deficiency in human skin.

BRIEF DESCRIPTION OF THE DRAWINGS

The accompanying drawings illustrate embodiments of the invention and, together with a general description of the invention given above, and the detailed description given below, serve to explain the invention.

DETAILED DESCRIPTION

While the specification concludes with claims that particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level, and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "charge density", as used herein, refers to the ratio of the number of positive charges on a monomeric unit of which a polymer is comprised to the molecular weight of said monomeric unit. The charge density multiplied by the polymer molecular weight determines the number of positively charged sites on a given polymer chain.

The term "epidermal skin model" or "3D epidermal skin model" means an EST1000 (Epidermal Skin Test) which is commercially available from CellSystems®. It is a three dimensional reconstructed human epidermis model. It consists of normal primary human epidermal keratinocytes. The cellular structure of EST1000 resembles that of the fully differentiated natural epidermis showing a base membrane, proliferating keratinocytes and a stratum corneum with an intact barrier function.

The term "personal care composition" as used herein, unless otherwise specified, refers to the compositions of the present invention, wherein the compositions are intended to include only those compositions for topical application to the hair or skin, and specifically excludes those compositions that are directed primarily to other applications such as hard surface cleansing, fabric or laundry cleansing, and similar other applications not intended primarily for topical application to the hair or skin.

The term "polymer" as used herein shall include materials whether made by polymerization of one type of monomer or made by two (i.e., copolymers) or more types of monomers.

The term "solid particle" as used herein means a particle that is not a liquid or a gas.

The term "water-soluble" as used herein, means that the polymer is soluble in water in the present composition. In general, the polymer should be soluble at 25° C. at a concentration of at least 0.1% by weight of the water solvent, preferably at least 1%, more preferably at least 5%, most preferably at least 15%.

The term "water-insoluble" as used herein, means that a compound is not soluble in water in the present composition. Thus, the compound is not miscible with water.

Caspase-14

Caspases belong to a family of autocatalytic cysteine proteases which regulate many cellular processes. In normal human epidermis nine procaspases are expressed but only caspase-14 is fully processed into its active form. Unlike most other caspases, caspase-14 exhibits no apoptotic activity but is involved in the breakdown of filaggrin into free amino acids. Caspase-14 has been shown to have an important role in differentiation, skin hydration, and the photoprotective function of the stratum corneum. Additional background on Caspase-14 is well known in the art. See Presland, Richard B.: *Function of Filaggrin and Caspase-14 in Formation and Maintenance of the Epithelial Barrier. Dermatol Sinica*: March 2009.

Using specific cosmetic ingredients to activate or protect caspase-14 expression in human skin, and in particular, treating human skin which is deficient in caspase-14, it has been discovered that benefits including improved hydration characteristics of skin, controlling the terminal differentiation process and stratum corneum formation, strengthening the skin barrier and protection against (external) stress such as UV irradiation may be conferred.

It has been discovered that using particular plant extracts in a cosmetic composition improves caspase-14 expression in human skin. Particular extracts include, for example, one or more extracts selected from the group consisting of *litchi*, glasswort, peach, soja seed, sweet basil, cucumber, chanterelle, leek, kiwi fruit, rhubarb, grapefruit, wheat, raspberry, plum, and mixtures thereof. In a preferred embodiment, the extracts are selected from *litchi* (also known as *litchi chinensis*) seeds and glasswort (also known as *salicornia herbacea*). The extract may be present in the composition in amounts ranging from about 0.0001-75%, preferably from about 0.0005-50%, and most preferably from about 0.001-10% by weight of the composition.

The *litchi* (*Litchi Chinensis*) is the sole member of the genus *Litchi* in the family of the Sapindaceae. Besides the *Litchi chinensis* subsp. *Chinensis*, there exist two other subspecies that could be considered for extraction: *Litchi chinensis* subsp. *philippinensis* (Radlk.) *Leenh* and *Litchi chinensis* subsp. *javensis*. Other varieties, forms, and cultivars in this genus are *L. chinensis* (Chinese Cherry), *L. chinensis* 'Brewster' (Lychee), *L. chinensis* 'Emperor' (Lychee), *L. chinensis* 'Hak Ip' (Lychee), *L. chinensis* javensis (Lychee), *L. chinensis* 'Kwai Mai Pink' (Lychee), *L. chinensis* 'Mauritius' (Lychee), *L. chinensis philippinensis*, *L. chinensis* 'Sweet Cliff' (Lychee), *L. chinensis* var. *euspontanea*, *L. litchi*, *L. philippinensis* and *L. sinensis*.

Other species in the genus *Salicornia* (glasswort) that could be considered for extraction are *Salicornia europaea*, (common glasswort), *S. bigelovii* (dwarf glasswort), *S. virginica* (American, Virginia or woody glasswort), *S. maritima* (slender glasswort), *S. ramosissima* (purple glasswort), *Arthrocnemum subterminale* (Parish's glasswort), *Eriogonum salicornioides* (glasswort buckwheat), *Tecticornia arbuscula* (shrubby glasswort) *T. flabelliformis* (bead glasswort), *T. pergranulata* (blackseed glasswort), *Salsola kali* (prickly glasswort), *Sarcocornia blackiana* (thick-head glasswort), *S. pacifica* (Pacific glasswort), *S. perennis* (perennial glasswort), and *S. quinqueflora* (beaded glasswort).

The present invention relates to cosmetic compositions comprising natural extracts which are effective for improving caspase-14 expression in human skin. This treatment is especially recommended for skin that is low in caspase-14 activity, such as Japanese, and by extension, Asian skin.

Figure 1:
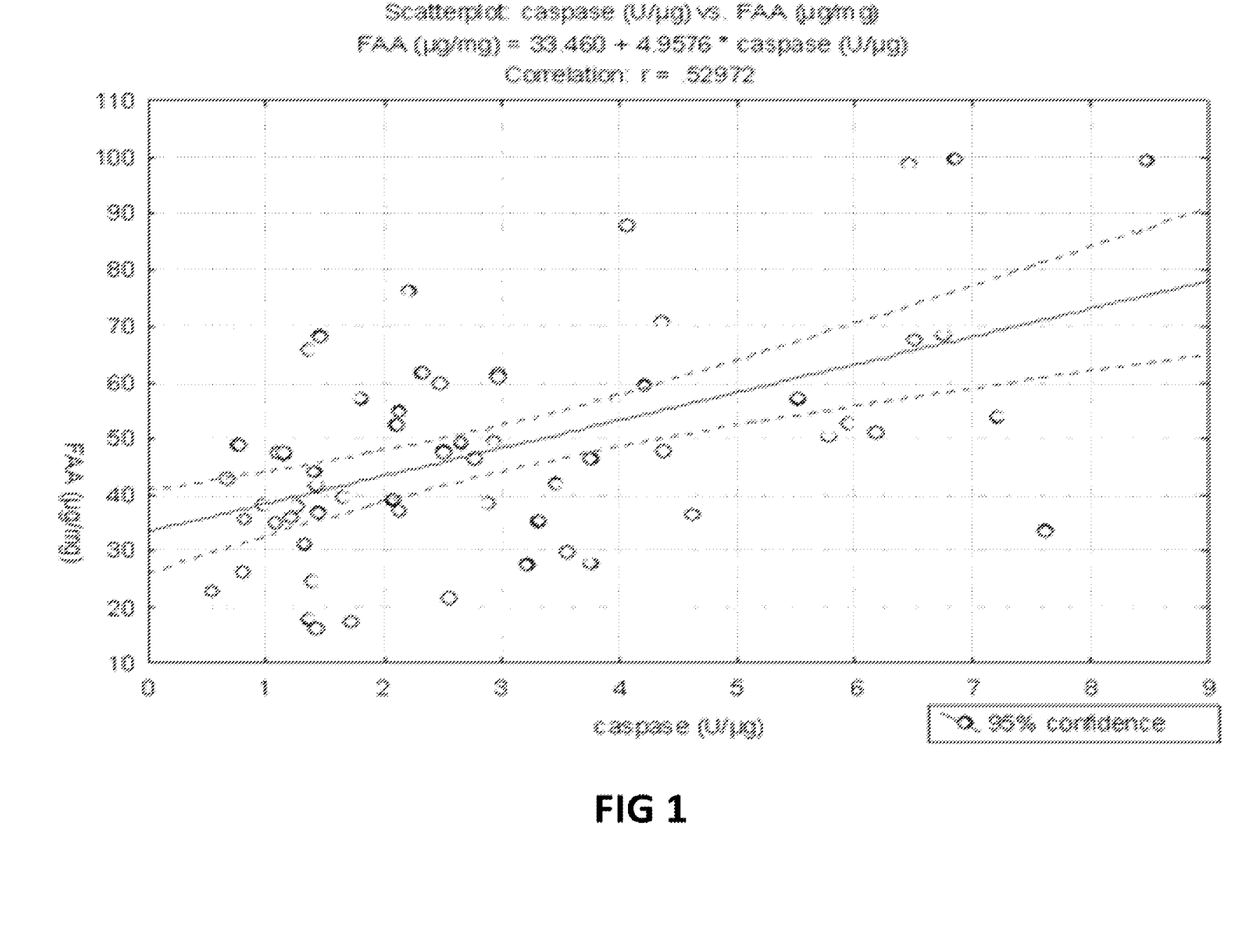
FIG. 1 is a graphical illustration of the direct relationship between the level of free amino acids on D-squame tape strippings and the level of stratum corneum caspase-14 enzyme activity.

Referring to FIG. 1, it is shown that caspase-14 activity is directly associated with free amino acid presence in skin. The measurement of caspase-14 enzyme activity on D-squame tape strippings was based on the enzymatic cleavage of the caspase-14 substrate Acetyl-L-tryptophyl-L-glutamyl-L-histidyl-L-aspartic acid α-(4-methyl-coumaryl-7-amide) with the release of the fluorogenic 7-amino-4-methylcoumarin ($\lambda_{Ex}$: 354 nm and $\lambda_{Em}$: 442 nm). The free amino acids were quantified after extraction from the D-squame tape strippings with a 0.5M borate buffer at pH 9.5. The concentration of the amino acids was determined by HPLC with a fluorescence detector after automated precolumn derivatization with ortho-phtaldialdehyde/3-mercaptopropionic acid.

Figure 2:
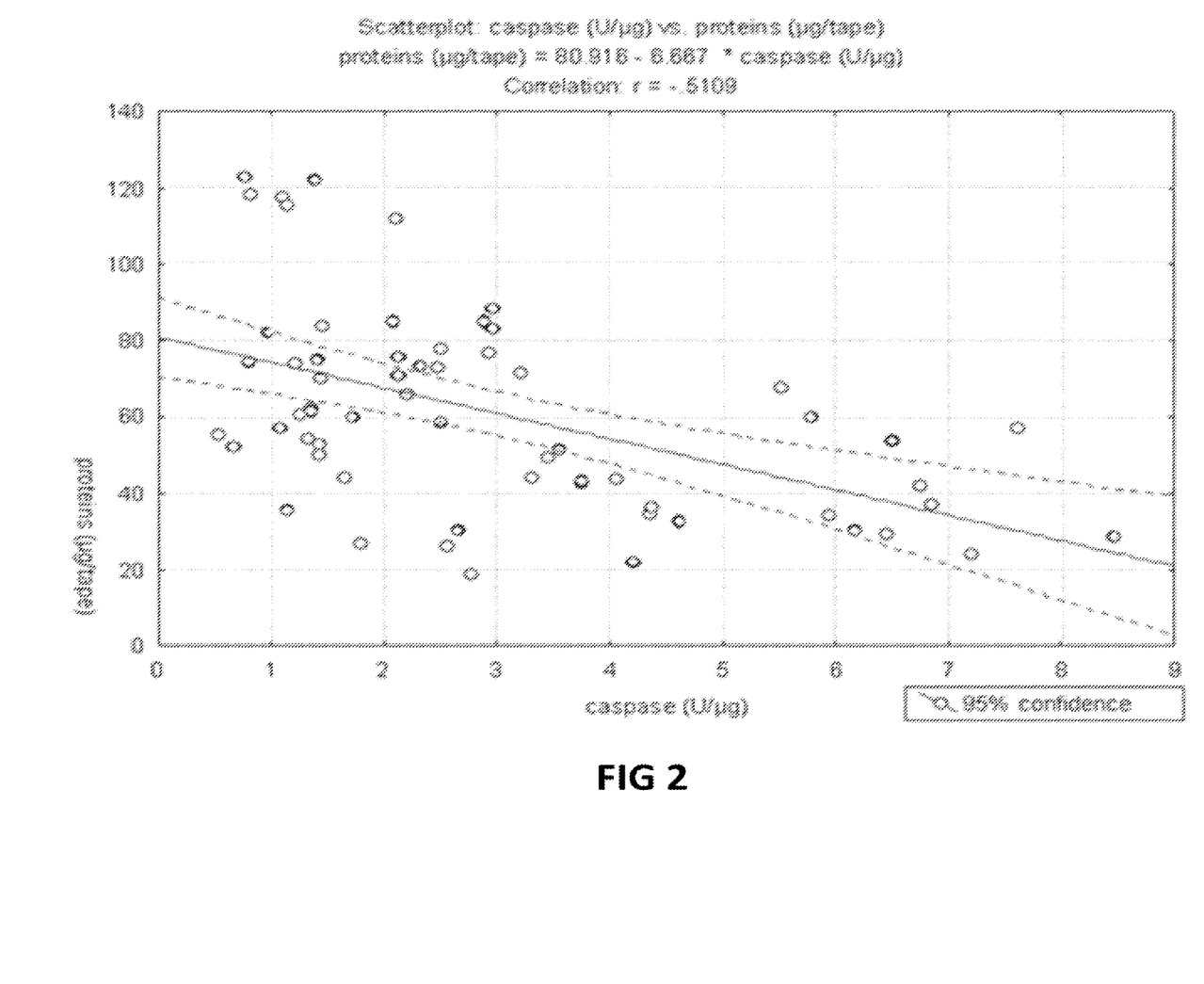
FIG. 2 is a graphical illustration of the inverse relationship between the level of proteins (~skin dryness) on D-squame tape strippings and stratum corneum caspase-14 enzyme activity.

FIG. 2 shows the inverse relationship between caspase-14 activity and protein concentration in skin. The total protein level on D-squame tape strippings were measured after complete hydrolyzation to amino acids at 120° C. for 20 hours with excess of HCl 6N. The amino acids were quantified as their isoindole derivatives, which are formed by reacting with orthoophtalaldehyde (OPA) in an alkaline medium in the presence of N-Acetyl-Cystein (NAC). These derivatives were detected by UV (335 nm) or fluorescence ($\lambda_{ex}$=340 nm, $\lambda_{em}$=445 nm). Increased protein levels are an indication of skin dryness. According to one embodiment of the present invention, caspase-14 deficiency may be identified by observing dryness of skin and/or eczema, or by observing low levels of free amino acids. Further, such deficiency may be localized to one or more skin zones. The term "skin zone" as used herein, means any area of the skin to which the composition herein may be applied, topically. The skin zone may be large (ie. the entire face), or localized to a specific skin area (ie. the elbow, cheek, eye lids, etc.).

Figure 3:
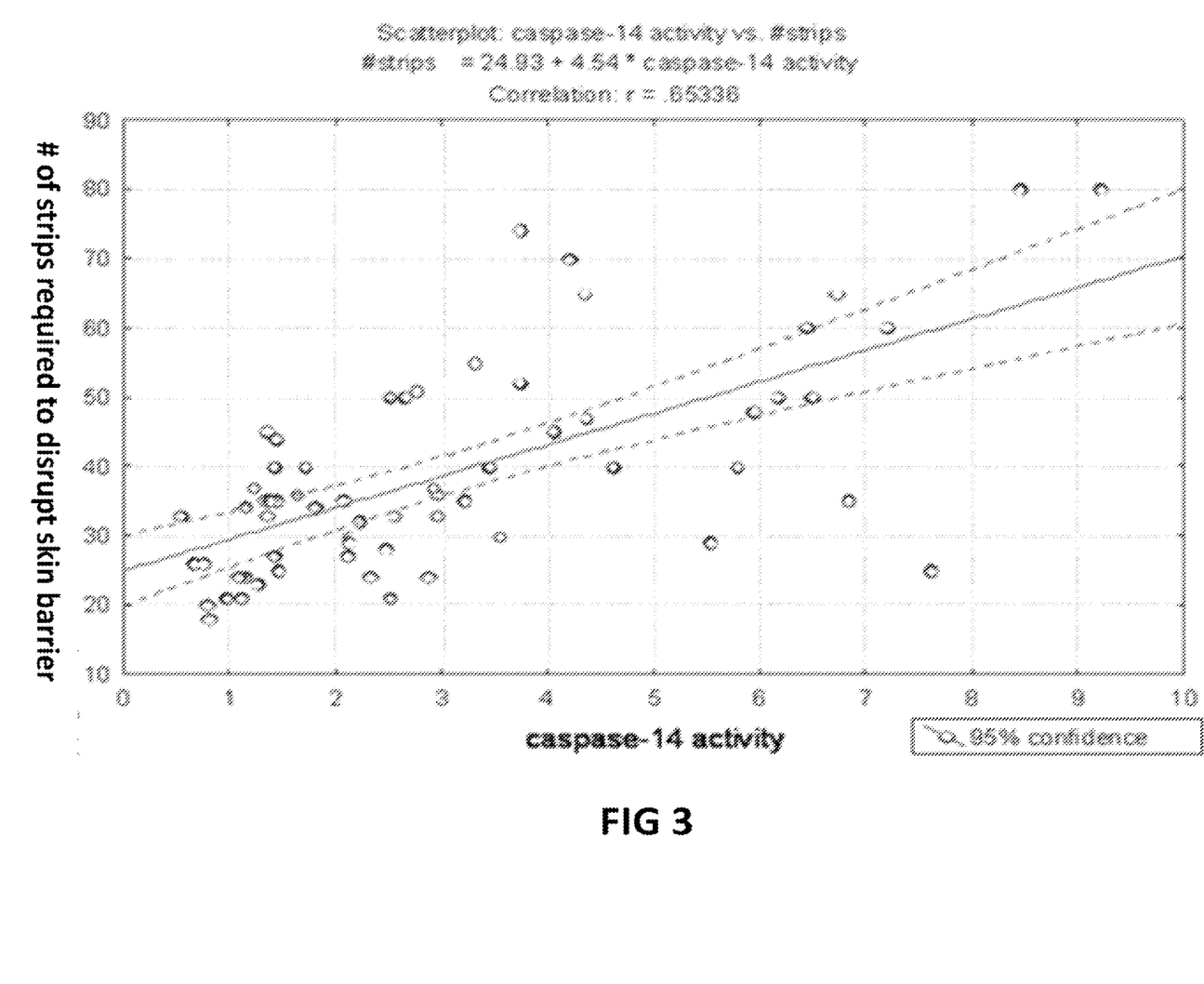
FIG. 3 is a graphical illustration of the direct relationship between skin barrier strength and stratum corneum caspase-14 enzyme activity.

Referring to FIG. 3, one benefit resulting from increased caspase-14 expression is improved skin barrier strength. Barrier strength was evaluated by challenging the skin of the ventral forearm of each panelist with tape stripping and measuring the trans-epidermal water loss (TEWL) with an instrument such as Tewameter® TM 300 (Courage-Khazaka) or Aquaflux AF200 (BIOX). The number of tape strippings required to reach a TEWL of 36 g/m²/hr is estimated for each panelist. The number of tape strippings required to perturb the barrier is a measure of its strength.

Figure 4:
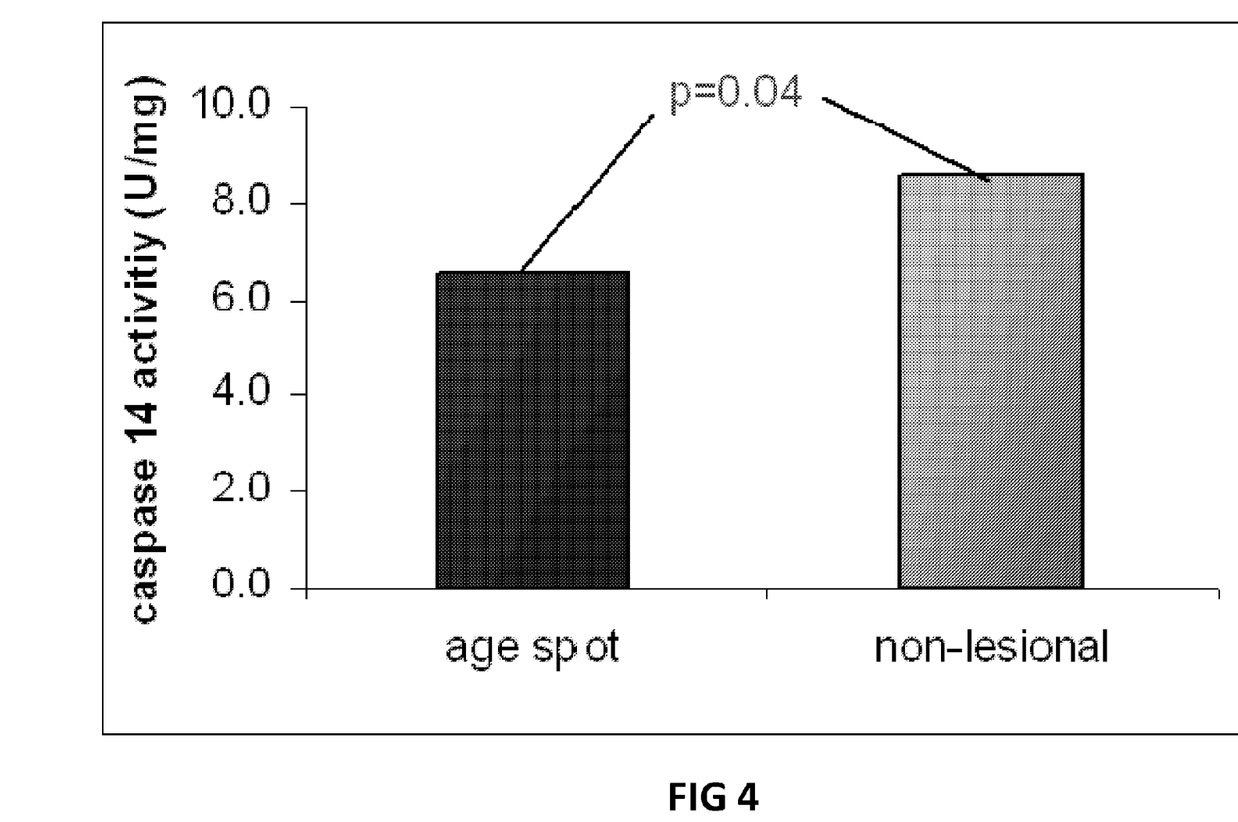
FIG. 4 is a graphical illustration comparing stratum corneum caspase-14 enzyme activity in solar lentigines of Caucasian skin and non-lesional Caucasian skin.
Figure 5:
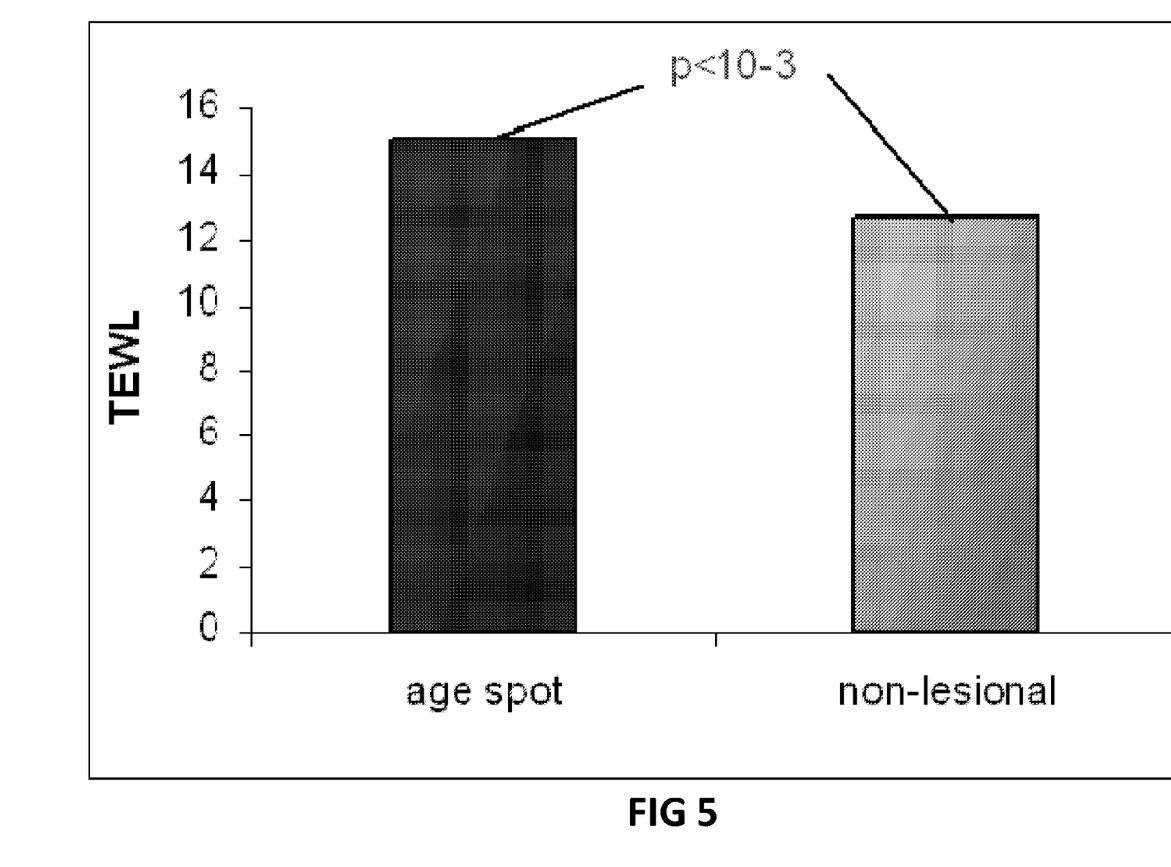
FIG. 5 is a graphical illustration of trans-epidermal water loss (TEWL) in solar lentigines of Caucasian skin versus non-lesional Caucasian skin.

Referring to FIGS. 4 and 5, it has been observed that caspase-14 activity is diminished in the presence of age spots (also often called liver spots, solar lentigines, or skin lesions). Twelve female Caucasian volunteers participated in a clinical study on age spots. Their mean age was 60 years with minimum and maximum of 48 and 70 years respectively. Ten consecutive small D-squame tape strippings (diameter 14 mm) were taken of an age spot and a non-lesional site. In total 24 lesional and non-lesional sites were investigated. Caspase-14 activity on the D-squame tape strippings was measured on layer 10. All data were normalized to the total protein amount on the D-squame tape strippings. In addition TEWL of the age spot and non-lesional site was registered with a Tewameter® TM 300 (Courage & Khazaka).

It is also shown that trans-epidermal water loss (TEWL) is increased in age spots compared to non-lesional sites. It is believed that increasing caspase-14 expression may prevent the appearance of such age spots as well as prevent TEWL in skin. Therefore, application of the compositions comprising extracts herein may prevent the appearance of age spots as a particular category of "signs of aging" in skin.

Figure 6:
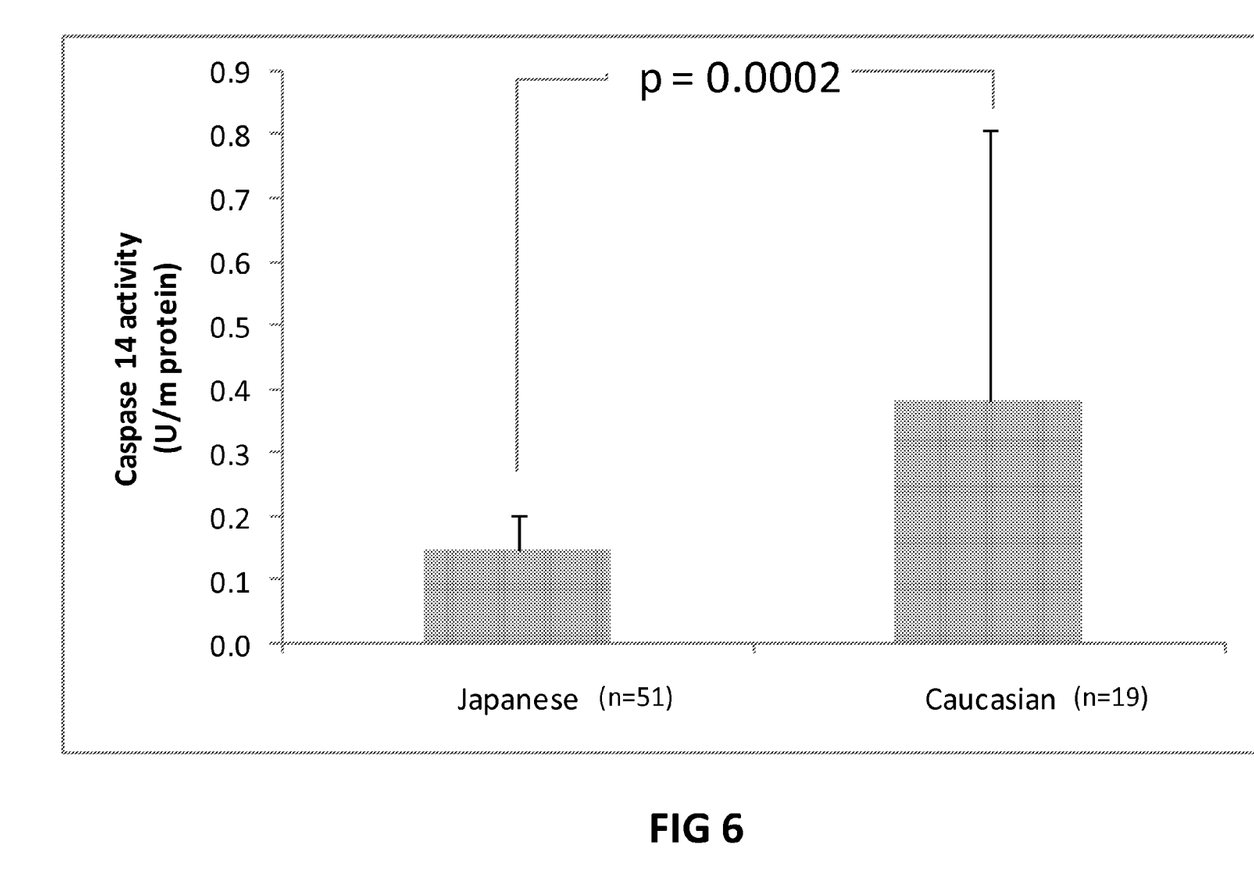
FIG. 6 is a graphical illustration comparing stratum corneum caspase-14 enzyme activity in Japanese skin compared to Caucasian skin.

Referring to FIG. 6, it has been discovered that caspase-14 activity is more typically decreased among specific ethnic skin types. As shown in FIG. 6, Asian, and particularly Japanese skin, has been found to generally have decreased levels of caspase-14 activity when compared to Caucasian skin. The total dataset consisted of 46 Caucasian and 57 Japanese panelists. The mean age of the Caucasians and Japanese was 46.8±13.8 and 52.3±12.0 years, respectively (minimum and maximum age was about 22 and 72). Untreated Caucasian samples and untreated Japanese samples were collected in Belgium and Japan respectively. Samples were collected by sequential tape stripping on the lower ventral part of the arm and stored at ~80° C. until analysis. Caspase-14 enzyme activity was analyzed on strip 9. The total protein amount was measured on the same tape stripping. Serine levels, as a measure for the total amount of free amino acids, histidine and UCA (cis and trans) were measured on tape stripping 7. All data were normalized to the total protein amount on the tape stripping. The ratio cis UCA to total UCA was used as a marker for recent sun exposure. Panelists with recent sun exposure were excluded from the dataset.

Figure 7:
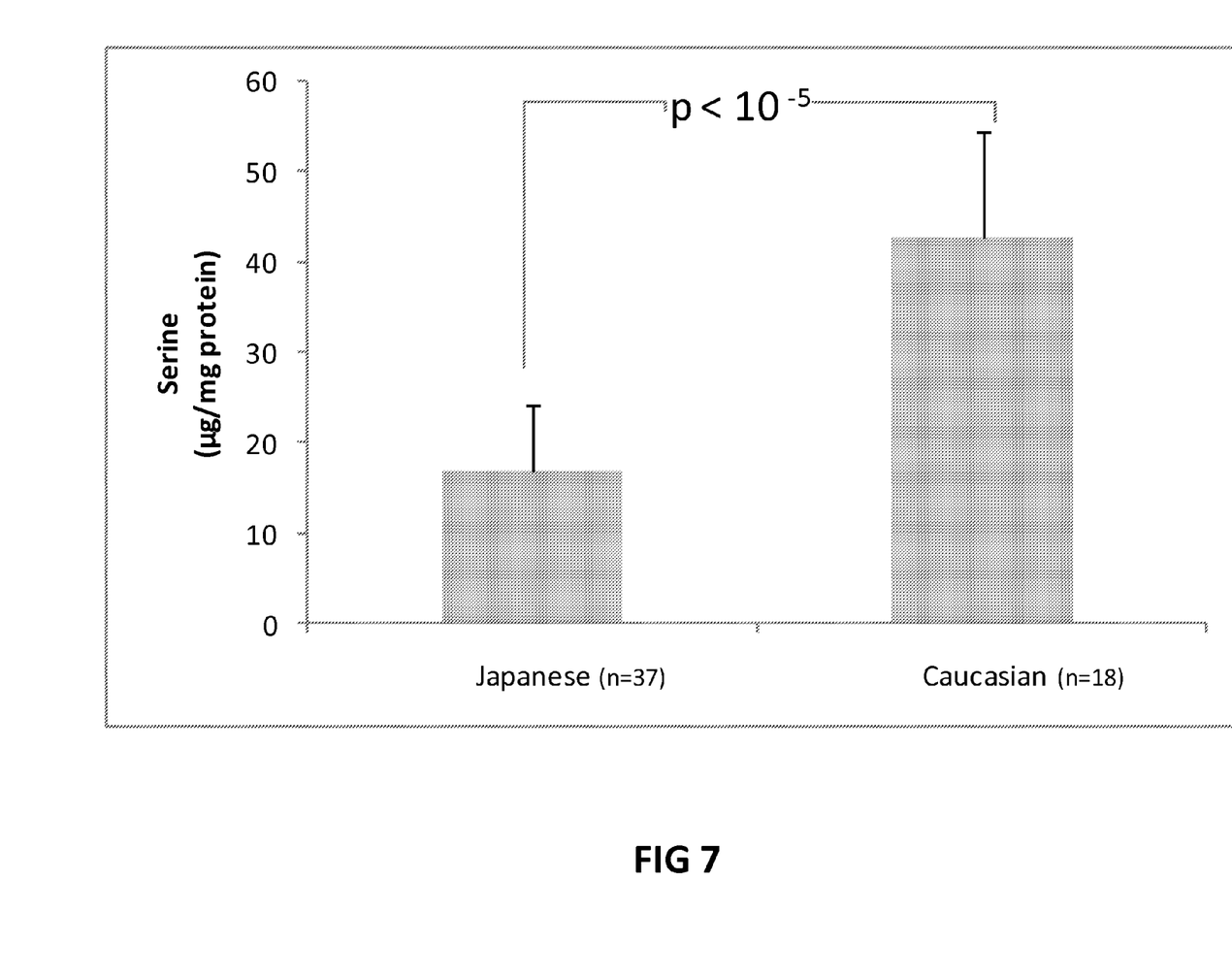
FIG. 7 is a graphical illustration comparing the level of free amino acids on D-squame tape strippings in Japanese and Caucasian skin.

FIG. 7 demonstrates lower free amino acid levels in Japanese compared to Caucasian skin Free amino acids were extracted from D-squame tape strips with 0.5M borate buffer at pH 9.5. The level of free amino acid was measured using an HPLC equipped with a fluorescence detector. All data were normalized to the total protein amount on the D-squame tape strippings.

Figure 8:
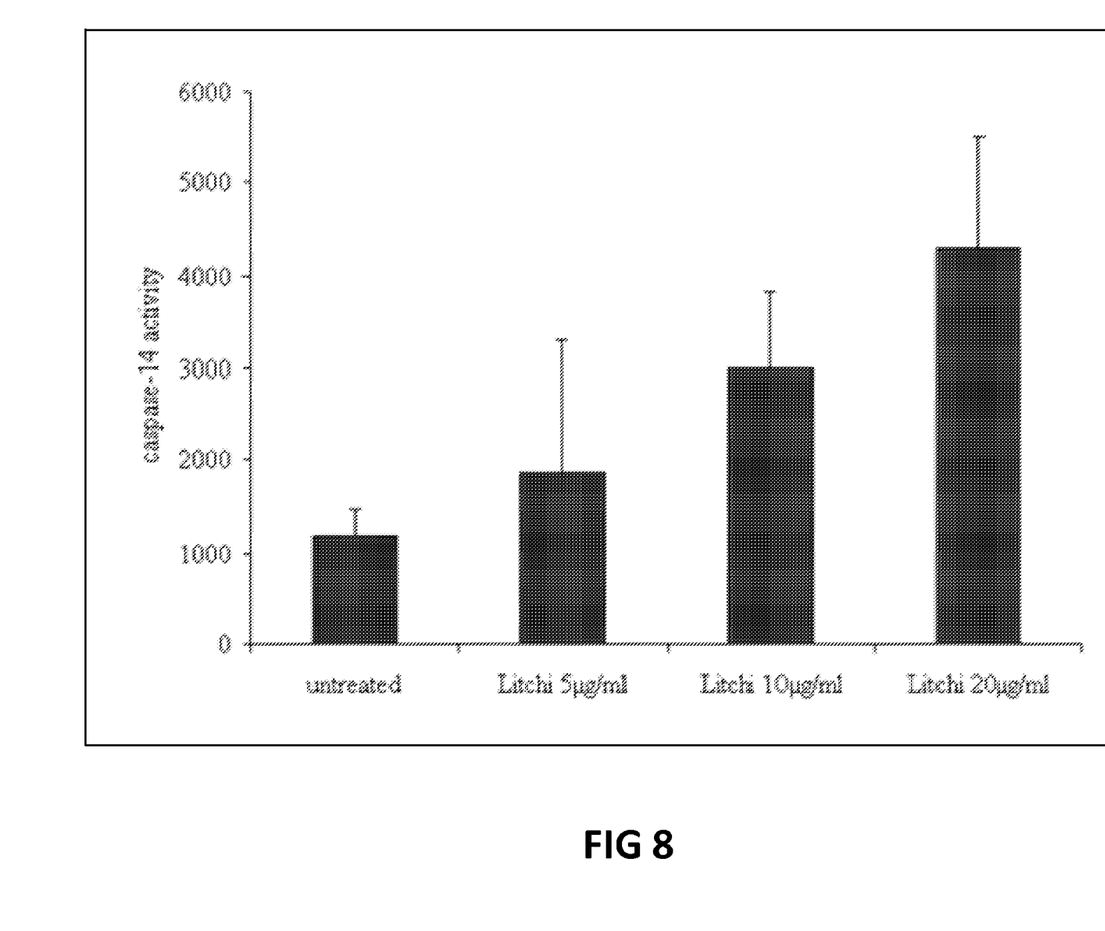
FIG. 8 is a graphical illustration of caspase-14 activity in 3D epidermal skin models after treatment with a *litchi* extract.

FIG. 8 is a graphical illustration of caspase-14 activity in 3D epidermal skin models after treatment with a *litchi* extract. Measurement of caspase-14 activity may be conducted according to the methods described hereinabove relating to FIGS. 1 and 2. Untreated skin is compared to skin which is treated with a solution containing *litchi* extract. Treatments are applied daily for 7 days. On the 7$^{th}$ day, caspase-14 activity is measured according to the methods described in FIGS. 1 and 2. Results of application of other extracts are further illustrated in Table 1.

Figure 9:
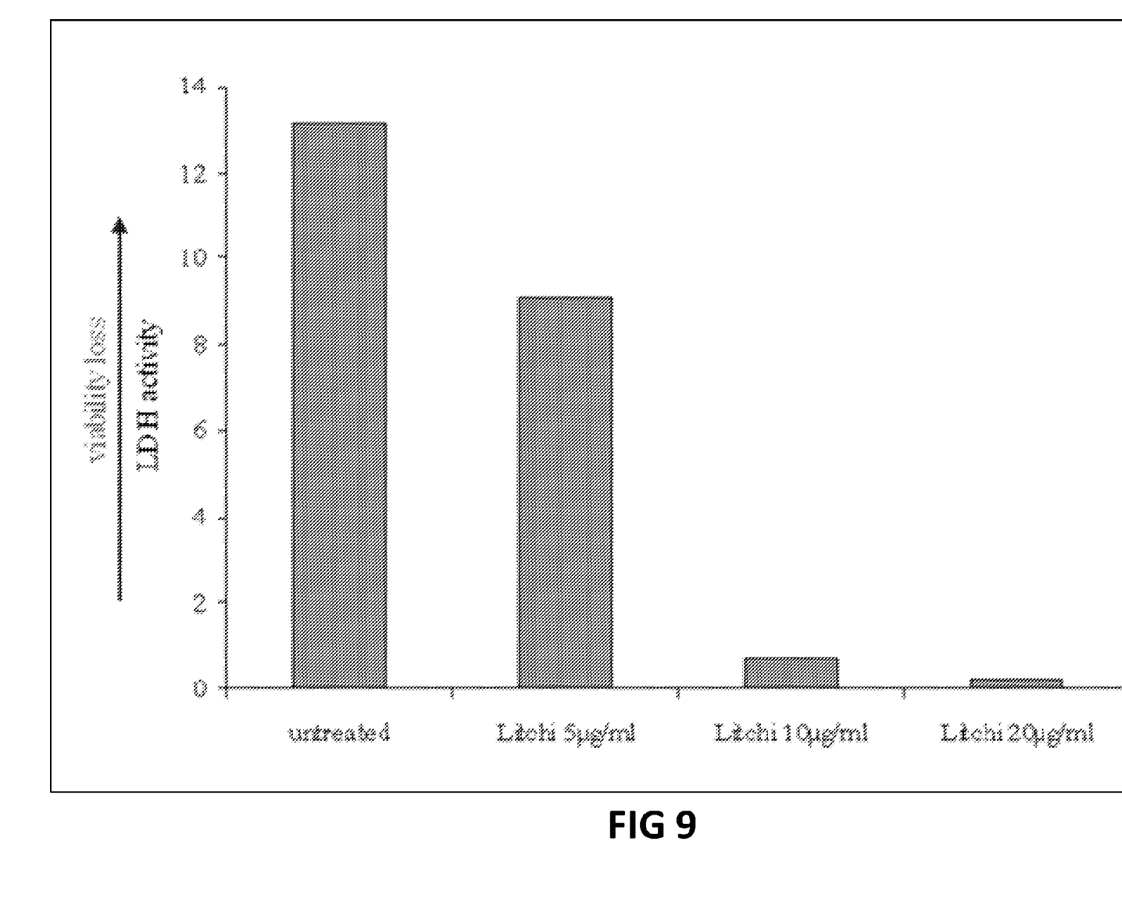
FIG. 9 is a graphical illustration of UV induced toxicity in 3D epidermal skin models, measured in terms of lactate dehydrogenase activity, in untreated skin, and skin treated with *litchi* extract.

FIG. 9 is a graphical illustration of UV induced toxicity in 3D epidermal skin models, measured in terms of lactate dehydrogenase activity, in untreated skin, and skin treated with *litchi* extract. Each 3D Epidermal Skin Model (EST1000; CellSystems) was treated during 7 days with or without the *Litchi* seed extract. The concentration of the extract was 5, 10 and 20 µg/ml in medium. Medium and extract were refreshed daily. After 7 days of treatment, the epidermal skin models were exposed to SSR (UVB: 0.4 J/cm²). After irradiation these models were placed in maintenance medium with or without the *litchi* seed extract for the next 24 hours, after which viability was measured using the lactate dehydrogenase (LDH) activity assay (Cytotoxicity Detection Kit (LDH)—Roche Applied Science Cat N° 11-644-793-001). This type of assay is based on the measurement of cytoplasmic enzyme activity released by damaged cells. LDH is a stable cytoplasmic enzyme present in all cells. It is rapidly released into the cell culture supernatant upon damage of the plasma membrane. The amount of enzyme activity detected in the culture supernatant correlates to the proportion of lysed cells.

Figure 10:
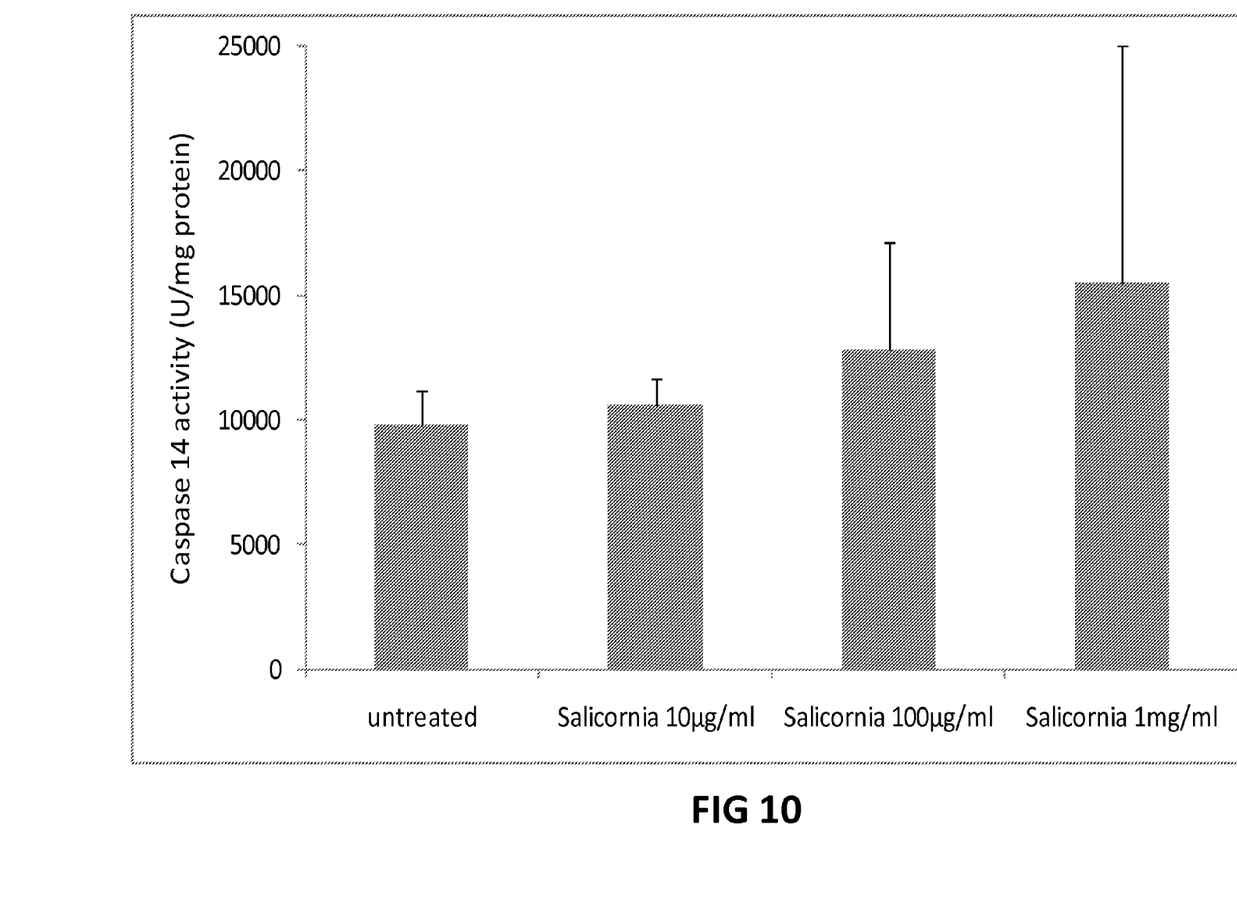
FIG. 10 is a graphical illustration of caspase-14 activity in 3D epidermal skin models after treatment with a *Salicornia herbacea* (glasswort) extract.

FIG. 10 is a graphical illustration of caspase-14 activity in 3D epidermal skin models after treatment with a *Salicornia herbacea* (glasswort) extract. This assessment is applied according to the procedure described according to FIG. 8.

DNA Repair Enzyme

The compositions may also contain one or more DNA repair enzymes. DNA repair enzymes may be present in an amount from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077, 211; 5,190,762; 5,272,079; and 5,296,231, are suitable for use in the compositions and method of the invention. One example of such a DNA repair enzyme may be purchased from AGI/Dermatics under the trade name Roxisomes®, and has the INCI name *Arabidopsis Thaliana* extract. It may be present alone or in admixture with lecithin and water. This DNA repair enzyme is known to be effective in repairing 8-oxo-diGuanine base mutation damage.

Another type of DNA repair enzyme that may be used is one that is known to be effective in repairing 06-methyl guanine base mutation damage. It is sold by AGI/Dermatics under the tradename Adasomes®, and has the INCI name Lactobacillus ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus lysate* (an end product of the controlled lysis of various species of *Micrococcus*), lecithin, and water. Photosomes® comprises a mixture of plankton extract (which is the extract of marine biomass which includes one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as *Bifida* lysate or *Bifida* ferment lysate, the latter a lysate from *Bifido* bacteria which contains the metabolic products and cytoplasmic fractions when *Bifido* bacteria are cultured, inactivated and then disintegrated. This material has the INCI name *Bifida* Ferment Lysate.

Other Ingredients

The composition may be in the form of an aqueous solution, gel, or suspension; or in the form of an emulsion—either water in oil or oil in water. The composition may also be anhydrous. The composition may be in the liquid, semi-solid, or solid form.

If present as an aqueous solution or dispersion, the amount of water present may range from about 0.01-99%, and the amount of dissolved or dispersed solids from about 10 to 99.99%.

If the composition of the invention is in the emulsion form, it may comprise from about 0.1-99% water and from about 0.1-80% oil.

If the composition of the invention is in an anhydrous form, it may contain from about 0.1-99% oil.

Sunscreens

The compositions of the subject invention may comprise one or more sunscreen actives (or sunscreen agents). Herein, suitable sunscreen actives include oil-soluble sunscreens, insoluble sunscreens, and water-soluble sunscreens. Non-limiting examples of suitable oil-soluble sunscreens are disclosed in The Cosmetic, Toiletry, and Fragrance Association's The International Cosmetic Ingredient Dictionary and Handbook, 10th Ed., Gottschalck, T. E. and McEwen, Jr., Eds. (2004), p. 2267 and pp. 2292-93 and include benzophenone-3, bis-ethylhexyloxyphenol methoxyphenyl triazine, butyl methoxydibenzoyl-methane, diethylamino hydroxybenzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof. Non-limiting examples of suitable insoluble sunscreens include methylene bis-benzotriazolyl tetramethylbutyl-phenol, titanium dioxide, zinc cerium oxide, zinc oxide, and derivatives and mixtures thereof. Non-limiting examples of suitable water-soluble sunscreens include phenylbenzimidazole sulfonic acid (PBSA), terephthalylidene dicamphor sulfonic acid, (Mexoryl™ SX), benzophenone-4, benzophenone-5, benzylidene camphor sulfonic acid, cinnamidopropyl-trimonium chloride, methoxycinnamido-propyl ethyldimonium chloride ether, disodium bisethylphenyl triaminotriazine stilbenedisulfonate, disodium distyrylbiphenyl disulfonate, disodium phenyl dibenzimidazole tetrasulfonate, methoxycinnamido-propyl hydroxysultaine, methoxycinnamido-propyl laurdimonium tosylate, PEG-25 PABA (p-aminobenzoic acid), polyquaternium-59, TEA-salicylate, and salts, derivatives and mixtures thereof.

Humectants

The composition may contain one or more humectants. If present, they may range from about 0.1 to 75%, preferably from about 0.5 to 70%, more preferably from about 0.5 to 40%. Examples of suitable humectants include glycols, sugars, and the like. Suitable glycols are in monomeric or polymeric form and include polyethylene and polypropylene glycols such as PEG 4-10, which are polyethylene glycols having from 4 to 10 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol, glycerin, propylene glycol, or hexylene glycol.

Botanical Extracts

It may be desirable to incorporate one more botanical extracts into the composition. If present suggested ranges are from about 0.0001 to 20%, preferably from about 0.0005 to 15%, more preferably from about 0.001 to 10%. Suitable botanical extracts include extracts from plants (herbs, roots, flowers, fruits, seeds) such as flowers, fruits, vegetables, and so on, including yeast ferment extract, *Padina Pavonica* extract, *Thermus Thermophilis* ferment extract, *Camelina Sativa* seed oil, *Boswellia Serrata* extract, olive extract, *Acacia Dealbata* extract, *Acer Saccharinum* (sugar maple), *Acidopholus, Acorus, Aesculus, Agaricus, Agave, Agrimonia*, algae, aloe, citrus, *Brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Prunus Amygdalus, Rosmarinus Officianalis, Sapindus makurossi, Caesalpinia spinosa, Citrus Medica Limonum, Panax Ginseng, Siegesbeckia Orientalis, Mangifera Indicia, Fructus Mume, Psidium Guajava, Ascophyllum Nodosum, Centaurium erythrea, Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus, Hordeum Vulgare, Cucumis Sativus, Evernia Prunastri, Evernia Furfuracea, Kola Acuminata*, glycyrretinic acid, and mixtures thereof.

Peptides

It may be desired to incorporate one or more peptides into the composition. The term "peptide" means from 2 to 20 amino acids connected by peptide bonds. If so, suggested ranges are from about 0.001 to 20%, preferably from about 0.005 to 15%, more preferably from about 0.01 to 10%. Preferred are biologically active peptides including those set forth in the C.T.F.A. International Cosmetic Ingredient Dictionary and Handbook, Eleventh Edition, 2006, page 2712. Such peptides include, but are not limited to the CTFA names: Acetyl Hexapeptide-1, 7, 8; Acetyl Pentapeptide-1, 2, 3, or 5; Acetyl Tripeptide-1; Acetyl Dipeptide-1 cetyl ester; Acetyl Glutamyl Heptapeptide-3; Acetyl Glutamyl Hexapeptide-6; Acetyl Monofluoropeptide-1; Heptapeptide-1, 2, or 3; Hexapeptide-1, 2, 3, 4, 5, 6, 7, 8, 9, 10, 11, 12, 13, or 14; Manganese Tripeptide-1; Myristoyl Hexapeptide-5, 12, or 13; Myristoyl Nonapeptide-2; Myristoyl Pentapeptide-4; Myristoyl Tetrapeptide-4 or 6; Myristoyl Tripeptide-4; Nisin, Nonapeptide-1 or 2; Oligopeptide-1, 2, 3, 4, 5, 6, 7, 8, 9 or 10; Palmitoyl Hexapeptide-14; Palmitoyl Pentapeptide-4; Palmitoyl Pentapeptide-4 or 5; Palmitoyl Tripeptide-1 or 5; Pentapeptide-1, 2, 3, 4, 5, or 6; Tetrapeptide-1, 2, 3, 4, 5, 6, or 7; Tripeptide-1, 2, 3, 4, or 5; or Palmitoyl Oligopeptides.

In one preferred embodiment the composition comprises Acetyl Hexapeptide-8, having the trade name Argireline®.

Oils

The composition may also comprise one or more oils in the form of natural, synthetic, or silicone oils. The term "oil" means that the ingredient is pourable at room temperature, e.g. 25° C. Oils may be volatile or non-volatile. The term "volatile" means that the oil has vapor pressure greater than about 2 mm of mercury at 20° C. The term "non-volatile" means that the oil has a vapor pressure of less than about 2 mm. of mercury at 20° C. If present, suggested ranges are from about 0.1 to 60%, preferably from about 0.5 to 45%.

Examples of volatile oils include volatile linear, cyclic or branched silicones such as cyclopentasiloxane, cyclohexasiloxane (2 cst), hexamethyldisiloxane (0.65 cst, centistokes), octamethyltrisiloxane (1.0 cst), decamethyltetrasiloxane (1.5 cst), or dodecamethylpentasiloxane (2.0 cst); or branched volatile silicones such as methyl trimethicone (1.5 cst). Also suitable are volatile paraffinic hydrocarbons such as isododecane, isohexadecane, C11-14 alkanes, and mixtures thereof.

Non-volatile oils include linear silicones commonly referred to as dimethicone; phenyl substituted silicones such as phenyl dimethicone, phenyl trimethicone, trimethylsiloxy phenyldimethicone, cetyl dimethicone, perfluorodimethicone, phenethyl dimethicone, and the like.

Non-volatile oils may also include esters or hydrocarbons. Esters include C1-10 alkyl esters of C1-20 carboxylic acids. One preferred type of ester is a fatty acid (C6-22) ester of a straight or branched chain saturated or unsaturated C1-22 alkyl. Examples include esters that have a low viscosity, e.g. ranging from 10-100 cst at room temperature. Examples of such esters include but are not limited to jojoba esters.

Other non-volatile oils include sterols such as phytosterols, phytosphingosine, and similar plant sterols.

Thickeners

Suitable thickeners may be incorporated into the composition. If so, suggested ranges are from about 0.0001-45%, preferably from about 0.0005-40%.

Examples of thickeners include animal, vegetable, mineral, silicone, or synthetic waxes which may have melting points ranging from about 30 to 150° C. including but not limited to Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, Japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

Also suitable as thickening agents are silicas, silicates, silica silylate, and alkali metal or alkaline earth metal derivatives thereof. These silicas and silicates are generally found in the particulate form and include silica, silica silylate, magnesium aluminum silicate, and the like.

Silicone elastomers may also be used as thickening agents. Such elastomers include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or a network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Coming's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the trade names KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crossoplymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK.

Polysaccharides may be suitable aqueous phase thickening agents. Examples of such polysaccharides include naturally derived materials such as agar, agarose, alicaligenes polysaccharides, algin, alginic acid, acacia gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

Also suitable are different types of synthetic polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. Acrylic polymer solutions include those sold by Seppic, Inc., under the tradename Sepigel® or those sold under the tradename Aristoflex®.

Also suitable are acrylic polymeric thickeners that are copolymer of A, B, and C monomers wherein A and B are as defined above, and C has the general formula:

wherein Z is —$(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

$CH_2=CR'CH_2OB_nR$ in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl(meth)acrylate, divinylbenzene, (poly)ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 allyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

One particularly suitable type of aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

Also suitable as thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CTFA names polyglycerin-20, polyglycerin-40, and the like.

Surfactants

If desired, the compositions of the invention may contain one or more surfactants. This is particularly desirable when the composition is in the form of an aqueous gel or emulsion. If present, the surfactant may range from about 0.001 to 50%, preferably from about 0.005 to 40%, more preferably from about 0.01 to 35% by weight of the total composition. Suitable surfactants may be silicone or organic, nonionic, anionic, amphoteric or zwitterionic. Such surfactants include, but are not limited to those set forth herein and are well known in the art.

Vitamins and Antioxidants

The compositions may comprise from about 0.0001% to about 50%, alternatively from about 0.001% to about 10%, alternatively from about 0.01% to about 5%, and alternatively from about 0.1% to about 1%, of one or more vitamins. Herein, "vitamins" means vitamins, pro-vitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, C1-C18 nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoid compounds such as retinol, retinyl acetate, retinyl palmitate, retinoic acid, retinaldehyde, retinyl propionate; carotenoids (pro-vitamin A); vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition comprises a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

Parabens

It is further recognized that there is an ongoing need for stable cosmetic systems which maximize the use of natural ingredients and therefore avoid negative side effects of certain synthetic preservatives. Accordingly, in one embodiment, the compositions are substantially free of parabens. Known parabens include butylparaben, ethylparaben, methylparaben, propylparaben, and mixtures thereof. The term, "substantially free" as used herein, means that less than 0.050%, and preferably no paraben materials are present in the composition.

Dermatologically Acceptable Carrier

The compositions comprise a dermatologically acceptable carrier for the skin care active materials. "Dermatologically acceptable," as used herein, means that the compositions or components described are suitable for use in contact with human keratinous tissue without undue toxicity, incompatibility, instability, allergic response, and the like. The compositions may comprise from about 50% to about 99.99%, alternatively from about 60% to about 99.9%, alternatively from about 70% to about 98%, and alternatively from about 80% to about 95% of the composition.

The carrier can be a wide variety of types, non-limiting examples of which include solutions, dispersions, emulsions and combinations thereof. Herein, "emulsions" generally contain an aqueous phase and an oil phase. The oils may be derived from animals, plants, or petroleum, may be natural or synthetic, and may include silicone oils. Emulsion carriers include, but are not limited to oil-in-water, water-in-oil and water-in-oil-in-water emulsions. In one embodiment, the carrier comprises an oil-in-water emulsion, a water-in-oil emulsion a silicone-in-water emulsion, and/or a water-in-silicone emulsion. The emulsions may comprise from about 0.01% to about 10%, and alternatively from about 0.1% to about 5%, of a nonionic, anionic or cationic emulsifier, and combinations thereof. Suitable emulsifiers are disclosed in, for example, U.S. Pat. No. 3,755,560, U.S. Pat. No. 4,421,769, and McCutcheon's Detergents and Emulsifiers, North American Edition, pages 317-324 (1986).

TABLE 1

| Sample name | % increase compared to non-treated skin model |
|---|---|
| Peach | 199.2 |
| *Litchi* | 198.4 |
| Soja seed | 179.2 |
| Sweet basil | 158.1 |
| Cucumber | 140.2 |
| Chanterelle | 129.5 |
| Leek | 128.6 |
| Kiwi fruit | 122.4 |
| Rhubarb | 122.1 |
| Grapefruit | 107.3 |
| Wheat | 105.8 |
| Raspberry | 103.7 |
| Plum | 100.8 |

Thirteen samples caused more than a doubling of caspase-14 enzyme activity in epidermal skin models (% activity > 100%) according to the method described in FIG. 8 above.
Note:
100% increase corresponds to a doubling of caspase-14 enzyme activity compared to the untreated epidermal skin model.

The invention will be further described in connection with the following examples which are set forth for purposes of illustration only.

EXAMPLES

A skin treatment serum is prepared as follows:

| Ingredient | A | B | C | D | E |
|---|---|---|---|---|---|
| Water | QS100 | QS100 | QS100 | QS100 | QS100 |
| Butylene glycol | 5.20 | 5.00 | 5.20 | 5.30 | 5.00 |
| Dimethicone | 4.25 | 2.00 | 2.80 | 3.25 | 4.25 |
| Acetyl hexapeptide-8 | 2.00 | 2.00 | 2.00 | 2.00 | 2.00 |
| Arginine/salicylic acid/tocopheryl acetate/mixed soy phospholipids | 2.00 | 2.00 | 2.00 | 2.00 | 2.00 |
| Jojoba esters | 1.50 | 1.50 | 1.50 | 1.50 | 1.50 |

-continued

| Ingredient | A | B | C | D | E |
|---|---|---|---|---|---|
| Glycerin | 1.25 | 1.25 | 1.25 | 1.25 | 1.25 |
| Dicaprylyl carbonate | 1.00 | 1.00 | 1.00 | 1.00 | 1.00 |
| Methyl trimethicone | 1.00 | 1.00 | 1.00 | 1.00 | 1.00 |
| Dimethicone/Polysilicone-11 | 1.00 | 1.00 | 1.00 | 1.00 | 1.00 |
| Water/*Prunus amygdalus ducis* (sweet almond) seed extract | 1.00 | 1.00 | 1.00 | 1.00 | 1.00 |
| Silica | 0.75 | 0.75 | 0.75 | 0.75 | 0.75 |
| Carbomer | 0.50 | 0.50 | 0.50 | 0.50 | 0.50 |
| Ammonium acryloyldimethyltaurate/VP copolymer | 0.50 | 0.50 | 0.50 | 0.50 | 0.50 |
| Glycerin/water/*Sapindus mukurossi* fruit extract/*Caesalpinia spinosa* gum | 0.50 | 0.50 | 0.50 | 0.50 | 0.50 |
| Butylene glycol/*Centaurium erythraea* (Centaury) extract | 0.50 | 0.50 | 0.50 | 0.50 | 0.50 |
| *Siegesbeckia Orientalis* extract/glycerin | 0.50 | 0.50 | 0.50 | 0.50 | 0.50 |
| Tromethamine | 0.45 | 0.45 | 0.45 | 0.45 | 0.45 |
| Phenoxyethanol | 0.43 | 0.43 | 0.43 | 0.43 | 0.43 |
| Caprylyl glycol/phenoxyethanol/hexylene glycol | 0.40 | 0.40 | 0.40 | 0.40 | 0.40 |
| Caffeine | 0.20 | 0.20 | 0.20 | 0.20 | 0.20 |
| Water/butylenes glycol/*Scutellaria baicalensis* (root) extract/*Pyrus Malus* (Apple) extract/*Cucumis Sativus* (cucumber) extract | 0.20 | 0.20 | 0.20 | 0.20 | 0.20 |
| Tetrahexyldecyl ascorbate | 0.20 | 0.20 | 0.20 | 0.20 | 0.20 |
| Phytosphingosine | 0.20 | 0.20 | 0.20 | 0.20 | 0.20 |
| *Litchi* extract | 0.00 | 0.0015 | 5.00 | 0.50 | 0.75 |
| Glasswort extract | 0.50 | 0.00 | 0.00 | 0.00 | 0.00 |
| Soja seed extract | 0.00 | 0.25 | 0.00 | 0.00 | 0.00 |
| Cucumber extract | 0.0015 | 0.20 | 0.00 | 0.00 | 0.00 |
| Fragrance | 0.15 | 0.15 | 0.15 | 0.15 | 0.15 |
| Glycyrretinic acid | 0.10 | 0.10 | 0.10 | 0.10 | 0.10 |
| *Mangifera Indicia* (Mango) leaf extract | 0.10 | 0.10 | 0.10 | 0.10 | 0.10 |
| *Psidium Guajava* (Guava) fruit extract | 0.10 | 0.10 | 0.10 | 0.10 | 0.10 |
| Zinc PCA | 0.10 | 0.20 | 0.10 | 0.10 | 0.10 |
| Zinc Pyrithione | 0.10 | 0.00 | 0.00 | 0.20 | 0.10 |
| *Polygonum cuspidatum* root extract | 0.05 | 0.05 | 0.05 | 0.05 | 0.05 |
| Sodium hyaluronate | 0.02 | 0.02 | 0.02 | 0.02 | 0.02 |
| Phosphatidyl choline | 0.009 | 0.009 | 0.009 | 0.009 | 0.009 |
| Sodium chloride | 0.009 | 0.009 | 0.009 | 0.009 | 0.009 |
| Phytosterol | 0.0019 | 0.0019 | 0.0019 | 0.0019 | 0.0019 |
| Disodium phosphate | 0.001 | 0.001 | 0.001 | 0.001 | 0.001 |
| Ursolic acid/*Rosmarinus Officinalis* (Rosemary) extract | 0.001 | 0.001 | 0.001 | 0.001 | 0.001 |
| *Anthemis Nobilis* (Chamomile) flower extract | 0.0005 | 0.0005 | 0.0005 | 0.0005 | 0.0005 |
| *Micrococcus Luteus* powder | 0.0005 | 0.0005 | 0.0005 | 0.0005 | 0.0005 |
| Potassium phosphate monobasic | 0.0002 | 0.0002 | 0.0002 | 0.0002 | 0.0002 |
| Potassium chloride | 0.0002 | 0.0002 | 0.0002 | 0.0002 | 0.0002 |
| Phosphatidyl ethanolamine | 0.00009 | 0.00009 | 0.00009 | 0.00009 | 0.00009 |
| Disodium EDTA | 0.00006 | 0.00006 | 0.00006 | 0.00006 | 0.00006 |
| BHT | 0.00002 | 0.00002 | 0.00002 | 0.00002 | 0.00002 |
| Oleic acid | 0.00002 | 0.00002 | 0.00002 | 0.00002 | 0.00002 |
| Sodium hydroxide | 0.000007 | 0.000007 | 0.000007 | 0.000007 | 0.000007 |
| OGGI fermentate | 0.000002 | 0.000002 | 0.000002 | 0.000002 | 0.000002 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating caspase-14 deficiency in the skin of a patient in need thereof consisting essentially of administering to the patient's skin a composition consisting essentially of therapeutically effective amounts of litchi extract, jojoba wax, and vitamin E.

* * * * *